United States Patent [19]

Lam et al.

[11] Patent Number: 5,583,029
[45] Date of Patent: * Dec. 10, 1996

[54] CULTURES FOR PRODUCTION OF AVERMECTIN AGLYCONES

[75] Inventors: Lapyuen H. Lam, Mystic; Hamish A. I. McArthur, Gales Ferry; Richard G. Wax, Waterford, all of Conn.

[73] Assignee: Pfizer Inc., New York, N.Y.

[*] Notice: The term of this patent shall not extend beyond the expiration date of Pat. No. 5,240,850.

[21] Appl. No.: 323,247

[22] Filed: Oct. 14, 1994

Related U.S. Application Data

[63] Continuation of Ser. No. 60,942, May 11, 1993, abandoned, which is a continuation of Ser. No. 660,972, Feb. 26, 1991, Pat. No. 5,240,850, which is a continuation of Ser. No. 112,972, Oct. 23, 1987, abandoned.

[51] Int. Cl.$^6$ ............... C12N 1/20; C12N 15/00; C12P 17/18
[52] U.S. Cl. ............... 435/253.5; 435/119; 435/172.1; 435/172.2; 435/76; 435/75; 536/7.1
[58] Field of Search ............... 435/253.5, 119, 435/172.1, 172.2, 76, 75; 536/7.1

[56] References Cited

U.S. PATENT DOCUMENTS

| | | | |
|---|---|---|---|
| 4,199,569 | 4/1980 | Chabala et al. | 424/180 |
| 4,206,205 | 6/1980 | Mrozik et al. | 424/180 |
| 4,285,963 | 8/1981 | Arison et al. | 424/279 |
| 4,310,519 | 1/1982 | Albers-Schonberg | 424/181 |
| 4,328,335 | 5/1982 | Mrozik | 536/7.1 |
| 4,333,925 | 6/1982 | Buhs et al. | 536/7.1 |
| 4,378,353 | 3/1983 | Goegelman et al. | 424/181 |
| 4,423,209 | 12/1983 | Mrozik | 536/7.1 |
| 4,429,042 | 1/1984 | Albers-Schonberg | 435/119 |
| 4,831,016 | 5/1989 | Mrozik | 514/30 |

FOREIGN PATENT DOCUMENTS

| | | |
|---|---|---|
| 1689 | 5/1979 | European Pat. Off. . |
| 2615 | 6/1979 | European Pat. Off. . |
| 7812 | 2/1980 | European Pat. Off. . |
| 214731 | 3/1987 | European Pat. Off. . |
| 215654 | 3/1987 | European Pat. Off. . |
| 58-78594 | 5/1983 | Japan . |
| 2166436 | 5/1986 | United Kingdom . |
| 2167751 | 6/1986 | United Kingdom . |
| 2176182 | 12/1986 | United Kingdom . |

OTHER PUBLICATIONS

Burg, R. W. et al., Antimicrob. Agents Chemother. 15:361–367 (1979).
Chen et al., Abstr. Pap. Am. Chem. Soc. 1983, 186 Meet. MBTD 28.
Cheremisinoff et al., *Biotechnology*, 1985, Technomic Publ. pp. 14–15.
Daum, S. J. et al., Ann. Rev. Microbiol. 33:241–265 (1979).
Fisher & Mrozik, *Macrolide Antibiotics*, Academic Press (1984), Chapter 14.
Gray, P. P. et al., J. Ferm. Technol. 50:381–387 (1971).
*Manual of Methods for General Microbiology*, P. Gerhardt, Editor-in-Chief, American Society for Microbiology, Washington, D.C., 1981, pp. 365–370.
Martin et al., J. Bacteriol. 115:198–204 (1973).
Ruby et al., 6th Int. Symp. on Actinomycete Biology, 1985, pp. 279–280.
Schulman et al., Antimicrobial Agents and Chemotherapy, 29:620–624 (1986).
Schulman et al., Antimicrobial Agents and Chemotherapy 31:744–747 (1987).
Schulman et al., Fed. Proc. 44:931 (1985).
Schulman et al., J. Antibiot. 38(11), 1494–1498 (1985).
Schulman, M. D. et al., J. Antibiotics 34:541–549 (1986).
Tabor et al., J. Bact. 128:485–486 (1976).
Willecke et al., J. Biol. Chem. 246:5264–5272 (1971).
Lehninger, A. L., *Short Course in Biochemistry*, Work Publishers, Inc., New York, NY (1973).

*Primary Examiner*—Irene Marx
*Attorney, Agent, or Firm*—Peter C. Richardson; Gregg C. Benson

[57] ABSTRACT

Mutants of *Streptomyces avermitilis* lacking ability to produce glycosylated avermectins and lacking branched-chain 2-oxo acid dehydrogenase activity, method for preparation thereof, and use thereof to produce natural and non-natural avermectin aglycones useful as parasiticides.

3 Claims, No Drawings

CULTURES FOR PRODUCTION OF AVERMECTIN AGLYCONES

CROSS REFERENCE TO RELATED APPLICATIONS

This is a continuation of application Ser. No. 08/060,942, filed May 11, 1993, now abandoned, which is a continuation of application Ser. No. 07/660,972, filed on Feb. 26, 1991, now U.S. Pat. No. 5,240,850, which is a continuation of application Ser. No. 07/112,972, filed on Oct. 23, 1987, now abandoned.

BACKGROUND OF THE INVENTION

1. Field of the Invention

This invention relates to mutants of *Streptomyces avermitilis* lacking the ability to produce glycosylated avermectins and lacking branched-chain 2-oxo acid dehydrogenase activity, to methods for producing said *S. avermitilis* and to their use for the production of natural and non-natural avermectin aglycones.

2. Description of the Prior Art

U.S. Pat. No. 4,310,519 and 4,429,042 describe the avermectins, a complex of related agents having potent antiparasitic activity, and their production by aerobic fermentation of strains of *Streptomyces avermitilis*; namely, *S. avermitilis* ATCC Nos. 31267, 31271 and 31272. The last two strains cited represent a frozen vial and a lyophilized tube, respectively, of a culture obtained by ultraviolet irradiation of *S. avermitilis* ATCC 31267.

EP 214,731, published March 18, 1987, the counterpart of U.S. patent application Ser. No. 886,867, filed Jul. 16, 1986, discloses a number of compounds (referred to herein as non-natural avermectins) related to the natural or known avermectins but having a novel substituent group at the 25-position, and a process for their preparation by fermentation of an avermectin producing organism in the presence of certain specified carboxylic acids, or derivatives or precursors thereof. Also disclosed are the aglycones of said avermectins and their preparation by mild acid hydrolysis of the non-natural avermectins. The *S. avermitilis* organisms used to produce the said novel C-25 substituted avermectins are *S. avermitilis* ATCC 31267, 31271, 31272 and NCIB 12121. The latter organism, derived from *S. avermitilis* ATCC 31271, gives improved yields of the novel C-25 substituted avermectins when it is cultured in a semi-defined medium. Each of ATCC 31267, 31271, 31272 and NCIB 12121 may also produce, in addition to the novel C-25 substituted derivative, varying amounts of the known, or natural, avermectins wherein the 25-substituent is isopropyl or (S)-sec-butyl (1-methylpropyl).

The carbon skeleton of the avermectins (depicted in formula (I) below) is derived from acetates and propionates and the C-25 substituent of natural avermectins from L-isoleucine (R=(S)-sec-butyl) or L-valine (R=isopropyl) [Fisher and Mrozik, "Macrolide Antibiotics", Academic Press (1984) Ch. 14].

By "known" or "natural" avermectins is meant those avermectins produced by *S. avermitilis* ATCC 31267, ATCC 31271 and ATCC 31272 wherein the 25-position substituent is isopropyl or (S)-sec-butyl(1-methylpropyl). Avermectins wherein the 25-position substituent is other than isopropyl or sec-butyl (S-form) are referred to herein as novel or non-natural avermectins.

The strains of *S. avermitilis* cited in the above-mentioned patents produce a class of substances described generically therein as C-076. The class comprises eight distinct but closely related compounds described as C-076 A1a, A1b, A2a, A2b, B1a, B1b, B2a and B2b. The "a" series of compounds refers to the natural avermectin wherein the 25-substituent is (S)-sec-butyl and the "b" series to those wherein the 25-substituent is isopropyl. The designations "A" and "B" refer to avermectins wherein the 5-substituent is methoxy or hydroxy, respectively. Lastly, the numeral "1" refers to avermectins wherein a double bond is present at the 22–23 position; and numeral "2" to avermectins having a hydrogen at the 22-position and hydroxy at the 23 position.

In this application, the "a" and "b" identifiers have been dropped. Identifiers A1, A2, B1 and B2 have been retained to refer to non-natural avermectins having the structural features corresponding to those of the natural avermectins as noted above.

Generation of mutants devoid of branched-chain 2-oxo acid dehydrogenase activity has been reported for *Bacillus subtilis*, Willecke and Pardee, J. Biol. Chem. 246, 5264–72 (1971) and *Pseudomonas putida*, Martin et al., J. Bacteriology, 115 198–204 (1973), but not for Sterptomyces.

U.S. Pat. No. 4,206,205 describes monosaccharide and aglycone derivatives of C-076; i.e., C-076 derivatives in which one or both of the carbohydrate moieties of the disaccharide function 4-(alpha-L-oleandrosyl) alpha-L-oleandrose attached to C-13 of the macrolide ring has been removed by hydrolysis in an aqueous non-nucleophilic organic solvent in the presence of an acid, preferably sulfuric acid.

*S. avermitilis* Agly-1, a mutant strain which produces virtually only avermectin aglycones A1a and A2a is reported by Schulman et al. J. Antibiot. 38(11), 1494–1498 (1985). Also reported is the fermentation of *S. avermitilis* Agly-1 in the presence of sinefungin which caused increased production of avermectin aglycone B components. Likewise, *S. avermitilis* O8, a high producing strain for avermectins, when fermented in the presence of sinefungin as inhibitor of O-methyl transferases, resulted in production of avermectins lacking O-methyl groups on the aglycone at C-5 and in the oleandrose disaccharide moiety.

U.S. Pat. No. 4,378,353 describes C-076 related compounds and their preparation by cultivation of MA-5218, a mutant strain of *S. avermitilis* ATCC 31272, obtained therefrom by ultraviolet irradiation. The mutant is identified as ATCC 31780. The C-076 related compounds produced by said mutant have major structural differences from the C-076 compounds. All the products lack the C-076 furan ring. Additionally, in certain of the compounds reported, one or both of the oleandrose sugar moieties have been cleaved while in others the 5-position group was oxidized to a keto group.

Three classes of O-methyltransferase mutants of *S. avermitilis* that produce avermectins lacking O-methyl groups have been reported by Ruby et al., 6th International Symposium on the "Biology of Actinomycetes", Debrecen, Hungary, Aug. 26–30 (1985) and by Schulman et al, Antimicrobial Agents and Chemotherapy 31, 744–7 (1987). The first class produces primarily B avermectins due to their inability to methylate the C-5 hydroxyl of the macrocyclic lactone ring. The second class produces 3'-O, 3"-O-bis-demethylavermectins (avermectins lacking the O-methyl substituent at the 3 position of both oleandrose monosaccharide residues), and which are referred to as demethylavermectins. The third class is unable to methylate at any position.

Schulman et al., Fed. Proc. 44, 931 (1985) disclose increased production of B avermectins by fermenting *S. avermitilis* in the presence of substances such as sinefungin, S-adenosylethionine and S-adenosylhomocysteine which inhibit the methylation of the C-5 hydroxy group of the aglycone moiety by the enzyme avermectin B-O-methyltransferase. *Streptomyces avermitilis* mutants which lack O-methyltransferase activity and produce increased amounts of avermectin B components are also disclosed and referred to by Schulman et al. in Antimicrobial Agents and Chemotherapy 29, 620–624 (1986).

It has now been found that mutagenesis of *S. avermitilis* mutants which lack branched-chain 2-oxo acid dehydrogenase activity produces mutants which, when cultivated in an appropriate medium, provide avermectin aglycones. The mutants do not possess the ability to produce natural avermectin aglycones in the absence of added compound RCOOH wherein R is isopropyl or (S)-sec-butyl, or of a compound convertible to RCOOH during the fermentation process. Surprisingly and unexpectedly, however, the mutants have been found to produce avermectin aglycones, natural and non-natural, when fermented in the presence of an added compound R—COOH wherein R is isopropyl or (S)-sec-butyl, or other group disclosed herein, or of a precursor to said RCOOH. It is even more surprising that the herein described mutants, which are unable to degrade L-isoleucine or L-valine, are able to assimilate a wide variety of compounds into the avermectin biosynthetic pathway with production of non-natural avermectin aglycones free of the presence of natural avermectin aglycones.

Certain of the natural avermectin aglycones, A1a and A2a, are produced by *S. avermitilis* Aglyl-1 as noted above. However, they, along with the aglycones of the remaining natural avermectins are normally prepared by acid hydrolysis of the corresponding avermectin. This procedure necessitates isolation of the natural avermectins from their fermentation broths. While the natural avermectins have been isolated in substantially pure form (see U.S. Pat. No. 4,429,042) the methodology is, at best, laborious. The overall production of avermectin aglycones by this procedure is, therefore, even more laborious by reason of the added step of hydrolysis. The ability to choose to produce either natural or non-natural avermectin aglycones so as to minimize the number and complexity of the products, and by so doing to increase the purity of a chosen avermectin aglycone, and thereby to simplify separation procedures, is a desirable goal.

SUMMARY OF THE INVENTION

*S. avermitilis* strains lacking branched-chain 2-oxo acid dehydrogenase activity and capable of producing aglycones when fermented in a suitable nutrient medium are obtained by mutation of *S. avermitilis* strains lacking branched-chain 2-oxo acid dehydrogenase activity. The herein described mutants of this invention are unable to synthesize the natural avermectin aglycones except where the fatty acid, or a precursor thereto, bearing the isopropyl or sec-butyl (S-form) group is added to the medium in which the mutants are fermented. They are capable of producing natural and non-natural avermectin aglycones when fermented under aqueous aerobic conditions in a nutrient medium containing an appropriate primer acid or compound convertible thereto in the fermentation process. The requisite branched-chain 2-oxo acid dehydrogenase deficient strains, e.g.*S. avermitilis* I-3 (ATCC 53567) are produced by mutation of avermectin producing strains of *S. avermitilis* and especially by mutation of *S. avermitilis* ATCC 31267, ATCC 31271, ATCC 31272 or NCIB 12121.

The mutants, characterized by their lack of branched-chain 2-oxo acid dehydrogenase activity, are selected from amongst the mutagenized colonies on the basis of a $^{14}CO_2$ assay. In this procedure the absence of $^{14}CO_2$ evolution by a permeabilized colony from a substrate of $[^{14}C-1]$-2-oxoisocaproic acid or $[^{14}C-1]$-2-oxo-3-methylvaleric acid or $[^{14}C-1]$-2-oxo-3-methylbutyric acid indicates absence of branched-chain 2-oxo acid dehydrogenase activity. The thus-produced mutants are then subjected to a second mutation. They are then cultivated in an appropriate medium in the presence of an appropriate primer acid and the fermentation products checked by thin-layer chromatography (TLC) and/or high performance liquid chromatography (HPLC) for aglycones. Alternatively, as those skilled in the art will recognize, the doubly blocked mutants can be produced in the reverse order; i.e.; the branched-chain 2-oxo acid dehydrogenase block can be introduced as the second rather than the first step.

It was surprising and unexpected that the herein-described mutants lacking branched-chain 2-oxo acid dehydrogenase activity exhibited the ability to produce avermectin aglycones, especially non-natural avermectin aglycones. The inability of the mutants of this invention to produce the natural fatty acylcoenzyme A derivatives when grown on a conventional medium could have been a lethal mutation if membrane integrity depended upon said derivatives or if 2-oxo acid accumulation by the mutant led to cytotoxicity. Furthermore, the mutants would not have been expected to synthesize acetyl-CoA and propionyl-CoA from L-isoleucine and L-valine degradative metabolism as this requires the enzyme activity that the mutants are missing. The requirement for these acyl-CoA derivatives for avermectin biosynthesis, noted above, led to the expectation that the mutants might be severely impaired in non-natural avermectin aglycone production, which, surprisingly, was not the case.

The lack of 2-oxo acid dehydrogenase activity in the mutants described herein results in the prevention of branched-chain fatty acyl-CoA synthesis from the degradation of L-isoleucine and L-valine and, thereby, the synthesis of the natural avermectins. In like manner, it is expected that branched-chain amino acid transaminase-negative mutants of *S. avermitilis* would reduce and possibly prevent the ability to produce the natural avermectins. Such transaminase-negative mutants would not be able to synthesize branched-chain 2-oxo acids from isoleucine and valine via the normal route of transamination. The reduced availability of these 2-oxo acids, which are substrates for the active branched-chain 2-oxo acid dehydrogenase enzyme, can effectively prevent branched-chain fatty acyl CoA synthesis. Thus, the present invention also encompasses the use of such transaminase-negative mutants alone, and mutants in which both the branched-chain transaminase negative and 2-oxo acid dehydrogenase-negative mutations are combined.

The present invention also includes any organism, regardless of its appearance or physiological behavior, that may be developed by means of transformation, transduction, genetic recombination or some other genetical procedure, using a nucleic acid or an equivalent material from the herein described species, whereby it has acquired the characteristics of the herein described mutants.

The terms "avermectin" or "avermectins" as used herein refers to compounds having formula (I) below but wherein the 25-substituent (R) can be any group assimilable at said position by the S. avermitilis of this invention. Avermectin aglycones refers to formula (II) compounds wherein the disaccharide ether moiety, 4-(alpha-L-oleandrosyl)-alpha-L-oleandrosyloxy, at C-13 is replaced by OH.

The herein described mutants are highly valuable for producing non-natural avermectin aglycones by the processes disclosed and exemplified herein. They are especially valuable for production of preferred avermectin aglycones, i.e., formula (II) compounds wherein the C-25 substituent is $C_4$–$C_6$ cycloalkyl or cycloalkenyl, optionally substituted by $C_1$–$C_4$ alkyl group; 1-methylthioethyl, or a 5- or 6-membered oxygen or sulfur heterocyclic group, especially 3-thienyl or 3-furyl.

DETAILED DESCRIPTION OF THE INVENTION

Mutation of an avermectin-producing member of the species *Streptomyces avermitilis* is carried out according to known procedures using any of a variety of mutating agents including ultraviolet irradiation, X-ray irradiation, N-methyl-N'-nitro-N-nitrosoguanidine, ethylmethane sulfonate, nitrous acid and nitrogen mustards, e.g., N-methylbis(2-chloroethyl)amine, or like treatments. The mutagenesis can be conducted on spores or on a vegetative culture of *S. avermitilis* capable of producing natural avermectins, e.g., *S. avermitilis* ATCC 31272.

Following procedures well known to those skilled in the art, mutagenized colonies are selected on the basis of a biochemical assay method which permits screening of large numbers of randomly mutagenized bacterial colonies for $^{14}CO_2$ production from [$^{14}C$-1]-2-oxo acids (Tabor et al., J. Bact. 128, 485–486, 1976).

The methodology comprises growing the mutant colonies in the wells of a microtiter plate on a suitable nutrient medium, permeabilizing the cells with toluene followed by adding the [$^{14}C$-1]-2-oxo acid (e.g. 2-oxoisocaproic acid) to each well and checking the atmosphere above the fermentation for $^{14}CO_2$. Alternatively, [$^{14}C$-1]-2-oxo-3-methylvaleric acid, or [$^{14}C$-1]-2-oxo-3-methylbutyric acid can be used in place [$^{14}C$-1]-2-oxo-isocaproic acid. Production of $^{14}CO_2$ is conveniently checked for by placing moist $Ba(OH)_2$— saturated filter paper above the individual wells to trap any $^{14}CO_2$ released and detection of $Ba^{14}CO_3$, if any, by autoradiography. Mutants which lack branched-chain 2-oxo acid dehydrogenase activity give autoradiograms approximating those of blank controls; i.e., no $Ba^{14}CO_3$ is produced by the mutants The thus-obtained mutants are subjected to further mutagenesis using any of the above-mentioned mutating agents. Mutagenized colonies are selected for their ability to produce avermectin aglycones when cultivated in a suitable medium.

The morphological and cultural characteristics of the mutants of this invention are generally as described in U.S. Pat. No. 4,429,042, but with certain exceptions. The distinguishing characteristics of the mutants of this invention are their lack of branched-chain 2-oxo acid dehydrogenase activity, and their ability to produce avermectin aglycones when cultivated in a suitable medium as described herein. These characteristics result in the failure of the mutants to produce the natural avermectin aglycones when grown on a defined medium substantially free of fatty acids RCOOH wherein R is isopropyl or (S)-sec-butyl, or compounds convertible to said RCOOH during fermentation. A taxonomic investigation conducted by the American Type Culture Collection, confirmed that the characteristics of *S. avermitilis* I-3, the parental strain, itself a mutant (selected by the above $^{14}CO_2$ assay), bears a close relationship to those of the grandparental ATCC 31272 strain described in U.S. Pat. No. 4,429,042. However, mutant strain I-3 (ATCC 53567) forms significantly fewer spore chains than does ATCC 31272; whilst, in contrast to the description given by Merck for ATCC 31272 in U.S. Pat. No. 4,429,042, we are unable to detect growth of the mutants or of ATCC 31272 with sucrose as sole carbon source.

Mutant I-3 is deficient only in branched-chain 2-oxo acid decarboxylase activity. The doubly-blocked mutant S-2805, obtained by further mutation of I-3 and selected for its ability to produce avermectin aglycones bears a taxonomic relation to ATCC 31272, similar to that of mutant strain I-3.

*Streptomyces avermitilis* I-3, and S-2805 have been deposited under the terms of the Budapest Treaty in the American Type Culture Collection, Rockville, Md., a recognized depository affording permanence of the deposits and ready accessibility thereto by the public if a patent is granted on this application. They have been given the designation *Streptomyces avermitilis* ATCC 53567 and ATCC 53677, respectively. The deposits are available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganisms deposited will be irrevocably removed upon granting of the patent.

Each of *S. avermitilis* ATCC 31267, ATCC 31271, ATCC 31272 and NCIB 12121 produces the natural avermectins, formula (I) compounds

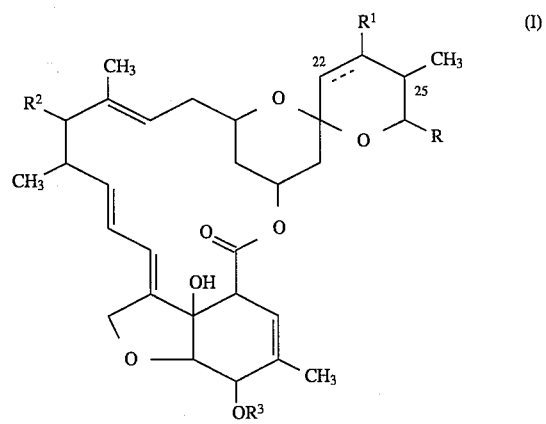

wherein
 the broken line at the 22–23 position represents an optional double bond;
 $R^1$ is hydroxy and is present only when the double bond is absent;
 $R^2$ is 4'-(alpha-L-oleandrosyl)-alpha-L-oleandrosyloxy of the formula

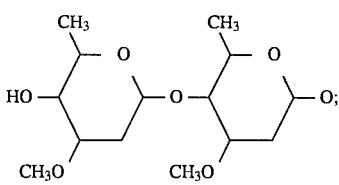

$R^3$ is hydrogen or methyl; and

R is isopropyl or (S)-sec-butyl. U.S. Pat. No. 4,285,963 describes an avermectin of formula (I) wherein the 25-position is substituted by a methyl and an ethyl group $R^1$ is hydroxy and $R^3$ is methyl.

In the non-natural avermectins referred to herein R is a substituent other than isopropyl or (S)-sec-butyl and is as defined below.

The mutants of this invention produce avermectin aglycones, formula (II); i.e. compounds of formula (I) but wherein $R^2$ is hydroxy. The value of R in the avermectin aglycones produced by the mutants of this invention can correspond to the group (isopropyl or (S)-sec-butyl) present in the natural avermectins, or to a group R wherein R is a group, other than isopropyl or (S)-sec-butyl, assimilable at the 25-position by the herein-described mutants.

The compounds L-valine and L-isoleucine essential for the biosynthesis of natural avermectins and their aglycones [formulae (I) and (II)] occur in the cell of S. avermitilis. These compounds are believed to enter into the biosynthesis of avermectins via conversion to 2-oxo acid and decarboxylation of the acid by branched-chain 2-oxo acid dehydrogenase, concomitant with coupling the product with coenzyme A. Their presence accounts for the concurrent production of both the isopropyl and (S)-sec-butyl compounds of formulae (I) and (II). This, of course, gives rise to problems in separating the isopropyl from the (S)-sec-butyl derivatives.

When fermented in a nutrient medium containing the appropriate primer compound the mutants of this invention produce a compound of formula (II) or, as is more usually the case, a mixture of two or more compounds of formula (II) in which R corresponds to the primer compound used. Up to four products, conveniently and trivially referred to as R-avermectin A1 aglycone, A2 aglycone, B1 aglycone and B2 aglycone, can be produced. The "R-" group, of course, refers to the C-25 substituent. For example, when R is cyclopentyl the four possible avermectin aglycones are:

| Trivial Name | $R^1$ | $R^3$ |
|---|---|---|
| cyclopentyl avermectin A1 aglycone | double bond | $CH_3$ |
| cyclopentyl avermectin A2 aglycone | hydroxy | $CH_3$ |
| cyclopentyl avermectin B1 aglycone | double bond | H |
| cyclopentyl avermectin B2 aglycone | hydroxy | H. |

In the non-natural avermectin aglycone the C-25 substituent "R" is other than isopropyl or (S)-sec-butyl.

Compounds of formula (II) wherein the double bond is present and OH is absent may alternatively be prepared from the corresponding compound of formula (II) wherein $R^1$ is OH and the double bond is absent by a dehydration reaction. The reaction is performed by first selectively protecting the hydroxy groups at the 5 and 13 positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration according to procedures described in U.S. Pat. No. 4,328,335. The product is finally deprotected to give the unsaturated compound.

Formula (II) compounds wherein $R^3$ is H may also be prepared from the corresponding compounds wherein $R^3$ $CH_3$ by demethylation. This reaction is achieved by treating the 5-methoxy compound, or a suitably protected derivative thereof, with mercuric acetate and hydrolyzing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209.

Compounds of formula (II) wherein $R^1$ is H and the double bond is absent can be prepared from the corresponding compound wherein the double bond is present and $R^1$ is absent, by selective catalytic hydrogenation using an appropriate catalyst. For example, the reduction may be achieved using tris(triphenylphosphine)rhodium (I) chloride as described in European Patent Application Publication No. 0001689.

The aglycones, formula (II), can also be prepared from the corresponding formula (I) compounds ($R^2$ is 4'-(alpha-L-oleandrosyl)-alpha-L-oleandrosyloxy) by removing the 4'-(alpha-L-oleandrosyl)-alpha-L-oleandrose group by mild hydrolysis with an acid in an aqueous organic solvent to yield the aglycone having a hydroxy group at the 13-position.

The compounds capable of utilization by the S. avermitilis of this invention for the biosynthesis of avermectins, natural and non-natural, are compounds of formula (III-A)

R—COOH            (III-A), including compounds convertible to (III-A) during the fermentation process. Said compounds are referred to herein as "primer compounds". In formula (III-A), R is an alpha-branched-chain group, the carbon atom thereof to which is attached the —COOH group is also attached to at least two other atoms or groups other than hydrogen. This definition, of course, embraces saturated and unsaturated acyclic and cyclic groups, including those optionally bearing a sulfur or oxygen heteroatom as a member of the acyclic chain or cyclic ring.

More specifically, R, which becomes the C-25 substituent, can be an alpha-branched $C_3$–$C_8$ alkyl, alkenyl, alkynyl, alkoxyalkyl or alkylthioalkyl group; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms (fluoro, chloro, iodo or bromo); or a 3 to 6 membered oxygen or sulfur containing heterocyclic ring which may be saturated, or fully or partially unsaturated and which may optionally be substituted by one or more $C_1$–$C_4$ alkyl groups or halo atoms.

Compounds convertible to RCOOH (III-A); i.e., precursors, in the fermentation process are compounds of formulae (III-B) wherein R is as defined above:

R—(CH$_2$)$_n$—Z            (III-B)

n is 0, 2, 4 or 6; and Z is —$CH_2OH$, —CHO, —$CH_2NH_2$, —$COOR^5$ or —$CONHR^6$ wherein $R^5$ is H or ($C_{1-6}$)alkyl;

$R^6$ is hydrogen, $(C_{1-4})$alkyl, or the residue of an amino acid, especially of aspartic acid, glutamic acid and methionine, e.g., —CH(COOH)CH$_2$COOH, —CH(COOH)(CH$_2$)$_2$COOH and —CH(COOH)(CH$_2$)$_2$SCH$_3$, respectively.

Also included in this invention are the isomeric forms of formula (III-A) and (III-B) compounds, and compounds convertible thereto during the fermentation process, and the isomeric avermectin aglycones at C-25 resulting from their use in the herein described process.

The process of this invention is carried out by aerobic fermentation with a strain of *S. avermitilis* which lacks ability to produce glycosylated avermectins and branched-chain 2-oxo acid dehydrogenase activity in an aqueous nutrient medium comprising an assimilable source of nitrogen, carbon, inorganic salts and a compound of formula RCOOH, or a compound convertible to said compound (i.e., a precursor) during the fermentation. The acid, or compound convertible thereto, is added to the fermentation either at the time of inoculation or at intervals during the fermentation. Production of the avermectin aglycone products may be monitored by removing samples from the fermentation, extracting with an organic solvent and following the appearance of the product by chromatography, for example using high performance liquid chromatography. Incubation is continued until the yield of the product has been maximized, generally for a period of from 4 to 15 days.

A preferred level of each addition of the primer compounds (carboxylic acid or compound convertible thereto) is between 0.05 and 3.0 grams per liter. The primer compound can be added continuously, intermittently or all at once to the fermentation. The acid (RCOOH) is added as such or as a salt, such as the sodium, lithium or ammonium salt, or as a compound convertible to the acid as defined above. The acid, if a solid, is preferably dissolved in a suitable solvent such as water or $(C_{1-4})$alcohols.

The media used for the fermentation can, especially when the C-25 substituent is to be isopropyl or (S)-sec-butyl, be conventional media containing assimilable sources of carbon, nitrogen and trace elements. When the C-25 substituent is to be a non-natural group; i.e., it is not isopropyl or (S)-sec-butyl, the fermentation medium is one in which the chosen ingredients lack, or contain only minimal amounts of primer compounds wherein the R moiety is isopropyl or (S)-sec-butyl.

After fermentation for a period of several days at a temperature preferably in the range of 24° to 33° C., the fermentation broth is centrifuged or filtered and the mycelial cake is extracted with preferably acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product is further purified as necessary by chromatography, for example using preparative reverse phase, high performance liquid chromatography.

The product is generally obtained as a mixture of the compounds of formula (II) wherein $R^1$ is OH and the double bond absent or $R^1$ is absent and the double bond is present and wherein $R^3$ is H or CH$_3$; however, the proportions can vary depending on the particular mutant and primer compound employed and the conditions used.

The source of the R group; i.e., whether it comes directly from R—COOH or is produced from one of the above precursors, or from any precursor, is immaterial to the production of the avermectin aglycones. The critical requirement of the process of this invention for their production is that the desired R group be made available to the *S. avermitilis* strains of this invention in the fermentation process.

Suitable compounds include the following:

2,3-dimethylbutyric acid
2-methylhexanoic acid
2-methylpent-4-enoic acid
2-cyclopropyl propionic acid
4,4-difluorocyclohexane carboxylic acid Lithium salt
4-methylenecyclohexane carboxylic acid
3-methylcyclohexane carboxylic acid (cis/trans)
1-cyclopentene carboxylic acid
1-cyclohexene carboxylic acid
tetrahydropyran-4-carboxylic acid
thiophene-2-carboxylic acid
3-furoic acid
2-chorothiophene-4-carboxylic acid
cyclobutane carboxylic acid
cyclopentane carboxylic acid
cyclohexane carboxylic acid
cycloheptane carboxylic acid
2-methylcyclopropane carboxylic acid
3-cyclohexene-1-carboxylic acid
2-methylthiopropionic acid
2-methyl-4-methoxybutyric acid
thiophene-3-carboxylic acid
hydroxymethylcyclopentane
3-thiophene carboxaldehyde
3-cyclohexylpropionic acid
3-cyclopentylpropionic acid
hydroxymethylcyclobutane
tetrahydrothiophene-3-carboxylic acid
3-cyclopentyl-1-propanol
3-methylcyclobutane carboxylic acid Lithium salt
3-fluorocyclobutane carboxylic acid
3-methylenecyclobutane carboxylic acid Lithium salt
2-methyl-4-methylthiobutyric acid
tetrahydrothiopyran-4-carboxylic acid
cyclobutylmethylamine
ethyl cyclobutanecarboxylate
4-hydroxymethylcyclopentene
2-(3-thiophenecarbonyl)propionic acid ethyl ester
S-2-methylpentanoic acid
R-2-methylpentanoic acid O-methyltransferase mutants can be obtained from the herein-described branched-chain 2-oxo acid dehydrogenase negative, aglycone-producing mutants. Mutations in active branched-chain 2-oxo acid dehydrogenase activity, combined with an O-methyltransferase mutation, yield strains of *S. avermitilis* that will, when fed RCOOH compounds or compounds convertible to RCOOH during the fermentation process, produce primarily B avermectins. Said mutants are obtained by mutagenesis of the herein described mutants which lack branched-chain 2-oxo acid dehydrogenase activity by means of ultraviolet light and/or chemical mutagens such as N-methyl-N-nitrosourethan, nitrosoguanidine or other agent such as those enumerated above. Alternatively, branched-chain 2-oxo acid dehydrogenase positive mutants which lack the O-methyltransferase can be mutated by treatment with UV light or a mutagenizing agent to produce the branched-chain 2-oxo acid dehydrogenase negative, aglycone-producing mutants.

In addition to production of desired alleles of a given strain of microorganism by mutagenesis, protoplast fusion permits introduction of desirable alleles produced/identified in one strain into the chromosome of another strain. For example, a strain of *S. avermitilis* deficient in branched-chain 2-oxo acid dehydrogenase activity and the ability to glycosylate avermectins can, by protoplast fusion with a 5-O-methyltransferase deficient *S. avermitilis* strain, produce a strain of *S. avermitilis* capable of synthesizing only avermectin B aglycones.

The non-natural avermectin aglycones produced by such mutants are characterized by the presence of hydroxy groups at the C-5 position of the aglycone moiety.

The above-described mutants are identified according to the methodology described by Schulman et al., Antimicrobial Agents and Chemotherapy, 29, 620–624 (1986). They are useful for the same purposes and in the same way as are the known avermectin aglycones.

Alternatively, increased amounts of the B avermectins are produced by fermenting the mutants of this invention, which lack active branched-chain 2-oxo acid dehydrogenase, in the presence of a substance such as sinefungin, S-adensylethionine or S-adensylhomocysteine which inhibits O-methyl transferase activity.

The compounds of the invention are highly active antiparasitic agents having particular utility as anthelmintics, ectoparasiticides, insecticides and acaricides.

Thus the compounds are effective in controlling; i.e., preventing and treating, a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of mammals (humans and animals) including, for example, Dirofilaria in dogs and various parasites which can infect humans including gastro-intestinal parasites such as Ancylostoma, Necator, Ascaris, Strongyloides, Trinchinella, Capillaria, Trichuris, Enterobius and parasites which are found in the blood or other tissues and organs such as filiarial worms and the extract intestinal states of Stronqyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (II) are administered as a formulation appropriate to the specific use envisaged and to the particular species of host animal being treated and the parasite or insect involved. For use as an anthelmintic the compounds may be administered orally in the form of a capsule, bolus, tablet or a liquid drench, or alternatively, they may be administered by injection or as an implant. Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. A drench formulation may be prepared by dispersing the active ingredient in an aqueous solution together with dispersing or wetting agents, etc., and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.02 to 10 mg per kg of animal body weight given as a single dose or in divided doses for a period of from 1 to 5 days will be satisfactory, but, of course, there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice. Production of *S. avermitilis* I-3 (ATCC 53567)

Step 1. *S. avermitilis* ATCC 31272 was grown as a confluent lawn on New Patch Agar Medium for 12 days at 30° C. The medium comprised

| | | |
|---|---|---|
| V-8 Juice* | | 200 ml |
| $CaCO_3$ | | 3 grams |
| Agar | | 15 grams |
| $H_2O$ | to | 1000 ml |
| Nutrient broth | | 1.0 grams/L |
| sodium acetate.$3H_2O$ | | 1.4 grams/L |
| isovaleric acid | | 50 mg/L |
| isobutyric acid | | 50 mg/L |
| 2-methylbutyric acid | | 50 mg/L |
| isoleucine | | 250 mg/L |
| leucine | | 250 mg/L |
| valine | | 250 mg/L |
| trace elements solution** | | 1 ml/L |

*A mixture of 8 vegetable juices (tomato, carrots, celery, beets, parsley, lettuce, watercress and spinach) plus salt, ascorbic and citric acids and natural flavors. Available from Campbell Soup Company, Camden, NJ.
**Composition of Trace elements solution:

| | |
|---|---|
| $FeCl_3.6H_2O$ | 2.7 g |
| $MnSO_4.H_2O$ | 4.2 |
| $CuSO_4.5H_2O$ | 0.5 |
| $CaCl_2$ | 11.0 |
| $H_3BO_3$ | 0.62 |
| $CoCl_2.6H_2O$ | 0.24 |
| $ZnCl_2$ | 0.68 |
| $Na_2MoO_4$ | 0.24 |

Dissolve the above in 1 liter of 0.1N HCl.

Spores were harvested from 3 such plates and suspended in 20 ml. of 0.05M tris-maleic acid buffer, pH 9.0.

Step 2. 10 ml of the spore suspension was added to a vial containing 10 mg of N-methyl-N'-nitro-N-nitrosoguanidine (NTG). The vial was incubated and shaken at 28° C. for 60 minutes and the spores then washed profusely with 1% NaCl solution.

Step 3. The washed spores were suspended in 1% NaCl and mixed with an equal volume of 80% ethylene glycol. This suspension was preserved at −20° C. and used as a source of cells to be screened for mutants. It gave approximately $10^4$ colonies/ml when germinated.

This spore stock was spread on YPD plates to yield approximately 100 colonies per plate (YPD medium comprises 10 g/l of each of yeast extract, Bacto peptone* and dextrose; and 15 g/l of Bacto agar*, adjusted to pH 6.9 before autoclaving) Ingredients marked with an asterisk are available from Difco Laboratories, Detroit, Mich. 48238.

step 4. Single colonies were picked from plates after 2–3 weeks of growth at 28° C. and placed in individual wells of a standard 96 well microtiter plate. Also, a small quantity of the colony was patched onto a fresh agar medium to serve as a source of viable cells when mutants are identified.

Step 5. To each well was added approximately 75 microliters of a liquid M9 salts medium containing 1% glucose, 0.1% casamino acids, and 0.01% of each of isovaleric, isobutyric and 2-methylbutyric acids. After several days of incubation at 28° C., the cells were assayed for the presence of branched-chain 2-oxo acid dehydrogenase. (Each liter of M9 salts medium comprises 6 g $Na_2HPO_4$, 3 g $KH_2PO_4$, 0.5 g NaCl and 1 g of $NH_4Cl$. The medium is autoclaved and then 1 ml of each of sterilized 1M $MgSO_4$ and 0.1M $CaCl_2$ are added aseptically).

Step 6. A microsuspension of 5% toluene in M9 salts medium was prepared by a brief sonication of the immiscible mixture. To 25 ml of this suspension was added 1.2 ml of a solution containing [$^{14}$C-1]-2-oxo-isocaproic acid, 2.5 microcurie/ml and 10.0 microcurie/micromole. 50 Microliters of this overall mixture was added to each of the wells of the microtiter plates containing the colonies to be assayed.

Step 7. The $^{14}CO_2$ produced from each well was trapped and visualized by the procedure described by Tabor et al., *J. Bacteriol.* 128 485–486 (1976) entitled "Convenient Method for Detecting $^{14}CO_2$ in Multiple Samples: Application to Rapid Screening for Mutants". Mutants lacking active branched-chain 2-oxo acid dehydrogenase produce no $Ba^{14}CO_3$ beyond that observed for the controls.

A more refined method which improves the contrast between a positive assay for $^{14}CO_2$, indicated by a dark spot on the autoradiogram as a result of $Ba^{14}CO_3$ formation, and a negative assay indicated by no spot or a very light spot, comprises the following modified screen.

Single colonies (see Step 4 above) were picked from the agar medium after 7–14 days of growth (rather than 2–3 weeks and assayed directly by steps 6 and 7 above). Step 5 of the above procedure is omitted.

An even more refined assay method which is quantitative in nature as regards $^{14}CO_2$ release comprises growing the mutants detected by the above screens on a suitable medium comprising M9 salts medium with glucose, 1% and "Syncasa-bcaa", 0.1% (a synthetic mixture of L-amino acids with the approximate composition of commercial casamino acids, but without the presence of L-valine, L-isoleucine and L-leucine, see below).

| Composition of "Syncasa - bcaa", 100 fold Concentrate | |
|---|---|
| | grams/liter |
| L-alanine | 3 |
| L-arginine | 4 |
| L-aspartic acid | 6 |
| L-cystine | 1 |
| L-glutamic acid | 20 |
| glycine | 1 |
| L-histidine | 2 |
| L-lysine | 7 |
| L-methionine | 3 |
| L-phenylalanine | 6 |
| L-proline | 10 |
| L-serine | 6 |
| L-threonine | 4 |
| L-tyrosine | 4 |
| L-tryptophan | 1 |

The mixture is adjusted to pH 7 and filter sterilized. One volume of concentrate is added to 99 volumes of medium to achieve standard use concentrations.

After growth to high cell density, the cells were washed in M9 salts medium and resuspended in cold M9 salts medium containing 1% toluene which had been sonicated to produce a milky white dispersion of the toluene. The cell/buffer/toluene suspension was incubated for 40 minutes at 30° C. in order permeabilize the cells. The permeabilized cells were then washed in M9 medium salts and finally resuspended in one-fifth the original volume of M9 medium buffer. 180 Microliters of this suspension were used per assay.

A reaction volume of 300 microliters contained the tolu-enized cells, thiamine pyrophosphate (TPP), 0.4 mM; coenzyme A (CoA), 0.11 mM; nicotinamide adenine dinucleotide (NAD), 0.68 mM, dithiothreitol (DTT), 2.6 mM; $MgCl_2$, 4.1 mM; Tris-HCl, 60 mM; Tris-HCl, 60 mM, pH 7.5; and [$^{14}$C-1]-alpha-ketoisocaproate, 6,000 cpm, microcurie per micromole. The efficiency of counting was 73%. The reaction was carried out in 15 ml scintillation vials containing a 2×2 cm Whatman #4 paper square pressed into the screw cap of the vial. The paper contains 30 microliters of 1M Hyamine Hydroxide (1M solution of methylbenzethonium hydroxide in methanol; available from Sigma Chemical Co., St. Louis, Mo. 63178), which traps $^{14}CO_2$ evolved in the reaction. After incubation for 2 hours, the papers are immersed in 10 ml of Beckman Aquasol II (Universal LSC (liquid scintillation counter) available from New England Nuclear Research Products, Boston, Mass. 02118) and the radioactivity measured in a liquid scintillation counter after equilibration in this solvent for 4 hours or more. A blank control reaction (i.e.—no cells) gives ca. 50–300 cpm.

Mutant I-3 and others like it gave counts that were less than or equal to the blank control reaction, whereas the parent strain gave counts several fold higher than the blank control value.

Isolation of *S. avermitilis* S-2805 (ATCC 53677)

Step 1. Approximately 100 mg of *S. avermitilis* I-3 (ATCC 53567), grown on a fresh SAMM agar plate for four days, was inoculated into a 300 ml flask containing 50 ml of SCM medium (pH 7.2). The flask was then shaken at 200 RPM and 30° C. for twenty-four hours (final pH=8.2).

Step 2. The flask was removed from the shaker and 10 ml of the whole broth centrifuged in a sterile tube for five minutes at 2000 RPM. The cells were then resuspended in 50 ml of SCM medium in sterile 300 ml. Erlenmeyer flasks and the flasks shaken on a rotary shaker for two hours at 30° C.

Step 3. The 10 ml of the suspension was placed in a sterile tube.

Step 4. Ethylmethane sulfonate was added to the tube (in a well ventilated hood), the contents thoroughly mixed, then poured into a sterile 300 ml flask and the flask shaken in a rotary shaker for three hours at 30° C.

Step 5. Fresh sterile SCM medium (40 ml) was added to the flask and shaking continued for a total of 70 hours at 30° C.

Step 6. The flask was removed, the contents spun down at 8000 RPM for ten minutes at 20° C. The cells were washed by re-suspending in SCM medium, spun down again and re-suspended in 10 ml SCM medium.

| SCM MEDIUM | |
|---|---|
| Yeast autolysate | 10 g/l |
| Beef extract | 5 g/l |
| Casein enzymatic hydrolysate | 10 g/l |
| 1M $MgSO_4$ | 3 g/l |
| 1M $K_2HPO_4$; pH 7.0 (HCl) | 100 g/l |

Step 7. The mutagenized population is diluted and spread for single colonies on SAMM agar.

SAMM Agar

|  | g/L |
| --- | --- |
| $Na_2HPO_4$ | 6.0 |
| $KH_2PO_4$ | 3.0 |
| NaCl | 0.5 |
| $NH_4Cl$ | 1.0 |
| 1M $MgSO_4$ | 1.0 |
| 0.1M $CaCl_2$ | 1.0 |
| Dextrose | 8.0 |
| Casamino Acids | 20.0 |
| Agar | 20.0 |

Step 8. Colonies of the mutagenized population (3% ethylmethane sulfonate) of *Streptomyes avermitilis* strain I-3 (ATCC 53567) are picked, and spread as patches on an agar medium prepared as follows (grams per liter): thinned starch, 80; $K_2HPO_4$, 1; $MgSO_4.7H_2O$, 1; ardamine PH, 5; $CaCO_3$, 5; P-2000, 1 ml; $FeSO_4.7H_2O$, 0.01; $MnCl_2.4H_2O$, 0.001; $ZnSO_4.7H_2O$, 0.001; Bacto agar, 17; distilled $H_2O$ to 980 ml. The pH is adjusted to 7.0 with NaOH prior to autoclaving at 121° C. for 20 minutes. After autoclaving, 20 ml of a sterile 5% stock solution of (±)-2-methylbutyric acid, pH 7.0 is added.

The agar cultures are incubated 8 to 12 days at 28° C. Cells (mycelia) are removed from the agar surface, and put into 250 microliters of acetone. Twenty-five (25) microliters of the acetone extracts are then spotted on Analtech Silica Gel GF precoated thin layer chromatography plates. The chromatogram is run for 30 to 40 minutes with ethyl acetate as solvent, then dried, and sprayed with 3% vanillin in ethanol. The plates are placed in a 100° C. oven for 1 to 3 minutes, then sprayed with 3% sulfuric acid in ethanol, and again placed in a 100° C. oven for 10 to 15 minutes. Aglycone-producing cultures are identified by the appearance of a novel spot (Rf ca. 0.63). This migrates coincident to A2 aglycone prepared by acid hydrolysis of A2a (1% $H_2SO_4$ in methanol, 25° C., 18 hours).

EXAMPLES 1–5

A frozen vial of culture *S. avermitilis* S-2805 (ATCC 53677) was inoculated into 100 ml of AS-7 medium in a 500 ml triple-baffled flask. The flask was incubated on a rotary shaker with agitation at 200 rpm at 28°–30° C. After 28 hours of incubation, 5 ml of the whole broth was inoculated into another 100 ml of AS-7 medium in 500 ml triple-baffle flask. The flask was again incubated on a rotary shaker with agitation at 200 rpm, at 28°–30° C. After 24 hours of incubation, 1 ml of the whole broth was inoculated into 300 ml flasks containing 40 ml of AP-5 medium.

Duplicate 40 ml fermentations were run at 28°–30° C. in the presence of 440 ppm of each of the primer compounds listed below. The time of addition of the primer compounds (RCOOH) to the fermentation is given in the right hand column.

| Primer Compound | Time of Addition |
| --- | --- |
| cyclohexane carboxylic acid | 24 hours |
| cyclopentane carboxylic acid | 96 hours |
| 3-thiophene carboxylic acid | 96 hours |
| 2-methylthiopropionic acid | 24 hours |
| 2-methylbutyric acid | 96 hours |

After 264 hours, the whole broth samples were diluted with water (10 mls) and extracted with methylene chloride (2×20 mls). The organic extract was dried ($MgSO_4$) and evaporated to dryness. The resulting residues were dissolved in methanol (1 ml) and 30 µl of solution injected onto a Beckman Ultrasphere ODS column (3.9 250 mm). The column was eluted with a mixture of methanol and 0.1M ammonium acetate (85:15) at a flowrate of 1 ml per minute. The column effluent was passed directly into a VG 12-250 thermospray mass spectrometer.

| Avermectin Aglycone | HPLC Ret. Time | Component Identity | Calcd. mol. wt. | Characteristic ions (m/e) |
| --- | --- | --- | --- | --- |
| sec-butyl | 5.69 | B2a | 602 | 603($MH^+$), 602($M^+$), 585 ($MH^+-H_2O$), 567 ($MH^+-2H_2O$) |
| sec-butyl | 6.56 | A2a | 616 | 634($MNH_3^+$), 617($MH^+$), 616($M^+$), 599($MH^+-H_2O$), 581($MH^+-2H_2O$) |
| sec-butyl | 8.39 | B1a | 584 | 585($MH^+$), 567($MH^+-H_2O$) |
| sec-butyl | 10.08 | A1a | 598 | 617($MNH_3^+$), 599($MH^+$), 581($MH^+-H_2O$) |
| cyclopentyl | 7.62 | 25-Cyclopentyl A2 | 628 | 646($MNH_3^+$), 629($MH^+$), 628($M^+$), 611($MH^+-H_2O$), 593($MH^+-2H_2O$) |
| cyclopentyl | 12.36 | 25-Cyclopentyl A1 | 610 | 628($MNH_3^+$), 611($MH^+$), 593($MH^+-H_2O$) |
| 3-thienyl | 5.43 | 25(3-Thienyl) A2 | 642 | 660($MNH_3^+$), 643($MH^+$), 642($M^+$), 625($MH^+-H_2O$) |
| 3-thienyl | 7.79 | 25(3-Thienyl) A1 | 624 | 642($MNH_3^+$), 625($MH^+$), 607($MH^+-H_2O$) |

AS-7 Medium

|  | g/l |
| --- | --- |
| thinned starch[a] | 20 |
| Ardamine pH[b] | 5 |
| Pharmamedia[c] | 15 |
| $CaCO_3$ | 2 |

[a]Prepared by hydrolysis of starch by alpha-amylase from *Bacillus licheniformis* (available from Novo Enzyme, Wilton, CT and sold under the trademark "Termamyl") to a dextrose equivalent of 40% + 5%
[b]From Yeast Products, Inc., Clifton, NJ 07012
[c]From Traders Protein, Memphis, TN 38108

Adjust pH to 7.2 with 25% NaOH.

| AP-5 Medium | |
| --- | --- |
| | g/l |
| thinned starch[a] | 80 |
| Ardamine pH[b] | 5 |
| $K_2HPO_4$ | 1 |
| $MgSO_4.7H_2O$ | 1 |
| NaCl | 1 |
| $CaCO_3$ | 7 |
| $FeSO_4.7H_2O$ | 0.01 |
| $MnCl_2.7H_2O$ | 0.001 |
| $ZnSO_4.7H_2O$ | 0.001 |
| P-2000 (antifoam) | 1 ml/l |

Adjust pH to 6.9 with 25% NaOH.

EXAMPLE 6

25-Cyclopentylavermectin A2 aglycone

A frozen inoculum (2 ml) of a culture of *Sterptomyces avermitilis* mutant organism ATCC 53677 was inoculated into 50 mls of a medium containing starch (1 g), Pharmamedia (Trademark) (0.75 g), ardamine pH (0.25 g), and calcium carbonate (0.1 g) in a 300 ml flask and incubated at 28° C. for 2 days. This inoculum (50 ml) was transferred to a second inoculum flask (600 ml) containing starch (12 g), Pharmamedia (8 g), ardamine pH (3 g) and calcium carbonate (1.2 g) and incubated at 28° C. for a further 2 days. This inoculum was used to inoculate 15 liters of a medium containing starch (1.5 kg), magnesium sulphate (15 g), Pharmamedia (75 g), dipotassium hydrogen phosphate (15 g), ferrous sulphate (0.12 g), calcium carbonate (105 g), glutamic acid (9 g, zinc sulfate (0.015 g) and manganous sulfate (0.015 g) contained in a 15 liter jar fermenter. The fermentation was incubated at 28° C., with agitation at 350 r.p.m. and aeration at 15 liters per minute. Cyclopentane carboxylic acid (6 g) was added after 96 hours and again after 216 hours (6 g). After 240 hours the mycelium was removed by filtration and extracted with acetone (5 L +0.75 L wash). The acetone extract was concentrated to approximately 1.5 L and extracted with ethyl acetate (3 L) in two portions. The resulting ethyl acetate layers were combined and evaporated to give a brown oil (1.2 g).

The above oil was dissolved in diethyl ether and added to a column of silica gel (40 g). The column was eluted with diethyl ether and 15 ml fractions were collected. Fractions 4–6 were combined and then evaporated to yield partially purified material (1.35 mg). The product was dissolved in methanol (0.5 ml) and chromatographed on a C18 Zorbax ODS (Trademark, Dupont) column (21 mm×25 cm) eluting with a mixture of methanol and water (75:25) at a flow rate of 9 mls per minute. The relevant fractions were combined and the solvent evaporated to yield the compound of formula (I) wherein $R^1$ is OH, the double bond is absent, $R^2$ is cyclopentyl, $R^3$ is $CH_3$ and $R^4$ is OH as a white powder (9 mg) m.p. 131°–133° C.

The structure of the product was confirmed by mass spectrometry as follows:

Fast atom bombardment mass spectrometry was performed on a VG Model 7070E mass spectromer using a sample matrix of triethylene glycol with solid sodium chloride. $(M+Na)^+$ observed at m/e 651 (theoretical 651).

Electron impact mass spectrometry was performed using a VG Model 7070F mass spectometer. The m/e values for the principal fragments were: 628 ($M^+$), 610, 468, 335, 317, 275, 251, 233, 223, 179.

We claim:

1. A biologically pure culture of *Streptomyces avermitilis* which produces only avermectin aglycones having an isopropyl or a (S)-sec-butyl group at C-25 when fermented in an aqueous nutrient medium comprising an assimilable source of carbon, nitrogen and inorganic salts under aerobic conditions only when said medium further comprises an acid of the formula R—COOH, or a precursor of said acid of the formula R-$(Ch_2)_n$—Z where n is 0, 2, 4 or 6; Z is —$CH_2OH$, —CHO, —$COOR^5$, —$CH_2NH_2$, or —$CONHR^6$ wherein $R^5$ is H or $(C_{1-6})$alkyl and $R^6$ is hydrogen, $(C_{1-4})$ alkyl, —CH (COOH) $CH_2COOH$, —CH (COOH) $(CH_2)_2COOH$ or —CH (COOH) $(CH_2)_2SCH_3$, wherein R is isopropyl or (S)-sec-butyl, said *S. avermitilis* lacking branched-chain 2-oxo acid dehydrogenase activity such that permeabilized cells thereof are unable to produce $^{14}CO_2$ from added [$^{14}C$-1]-2-oxo-isocaproic acid.

2. A biologically pure culture of *Streptomyces avermitilis* which produces only avermectin aglycones having an isopropyl or a (S)-sec-butyl moiety at C-25 upon fermentation in an aqueous nutrient medium comprising an assimilable source of carbon, nitrogen and inorganic salts under aerobic conditions only when said medium further comprises an acid of the formula R—COOH, or a precursor of said acid of the formula R-$(CH_2)_n$—Z where n is 0, 2, 4 or 6; Z is —$CH_2OH$, —CHO, —$COOR^5$, —$CH_2NH_2$ or —$CONHR^6$ wherein $R^5$ is H or $(C_{1-6})$alkyl and $R^6$ is hydrogen, $(C_{1-4})$alkyl, —$CH(COOH)CH_2COOH$, —$CH(COOH)$ $(CH_2)_2COOH$ or —$CH(COOH)$ $(CH_2)_2SCH_3$ wherein R is isopropyl or (S)-sec-butyl.

3. A strain of *Streptomyces avermitilis* which produces only avermectin aglycones having an isopropyl or a (S)-sec-butyl moiety at C-25 wherein (a) said strain is obtained by mutating *Streptomyces avermitilis* ATCC 53567; and (b) said strain, when fermented in an aqueous nutrient medium comprising an assimilable source of carbon, nitrogen and inorganic salts under aerobic conditions, produces only said avermectin aglycones having an isopropyl or a (S)-sec-butyl moiety at C-25 only when said medium further comprises an acid of the formula R—COOH, or a precursor of said acid of the formula R-$(CH_2)_n$—Z where n is 0, 2, 4 or 6; Z is —$CH_2OH$, —CHO, —$COOR^5$, —$CH_2NH_2$, or —$CONHR^6$ wherein $R^5$ is H or $(C_{1-6})$alkyl and $R^6$ is hydrogen, $(C_{1-4})$alkyl, —$CH(COOH)CH_2COOH$, —$CH(COOH)$ $(CH_2)_2COOH$ or —$CH(COOH)(CH_2)_2SCH_3$ wherein R is isopropyl or (S)-sec-butyl.

* * * * *

UNITED STATES PATENT AND TRADEMARK OFFICE
CERTIFICATE OF CORRECTION

PATENT NO.   : 5,583,029
DATED        : December 10, 1996
INVENTOR(S)  : Lapyuen H. Lam et al.

It is certified that error appears in the above-identified patent and that said Letters Patent is hereby corrected as shown below:

Column 2, line 23 - "Sterptomyces" should read -- Streptomyces --.

Column 7, line 13 - "group" should read -- group, --.

Column 17, line 21 - "*Sterptomyces*" should read -- *Streptomyces* --.

Column 17, line 49 - "(1.35 mg)" should read -- (135 mg) --.

Column 18, line 18 - "R-(Ch$_2$)$_n$-Z" should read -- R-(CH$_2$)$_n$-Z --.

Signed and Sealed this

Twentieth Day of May, 1997

Attest:

BRUCE LEHMAN

Attesting Officer    Commissioner of Patents and Trademarks